United States Patent [19]

McCleary et al.

[11] Patent Number: 5,234,825
[45] Date of Patent: Aug. 10, 1993

[54] PROCESS OF POLYSACCHARIDES

[75] Inventors: Barry V. McCleary, South Penrith, Australia; Peter Critchley; Paul V. Bulpin, both of Bedford, England

[73] Assignee: Unilever Patent Holdings, B.V., Rotterdam, Netherlands

[21] Appl. No.: 682,850

[22] Filed: Apr. 5, 1991

Related U.S. Application Data

[63] Continuation of Ser. No. 399,445, Aug. 28, 1989, abandoned, which is a continuation of Ser. No. 147,634, Jan. 25, 1988, abandoned, which is a continuation of Ser. No. 22,571, Mar. 4, 1987, abandoned, which is a continuation of Ser. No. 584,905, Feb. 29, 1984, abandoned.

[30] Foreign Application Priority Data

Mar. 11, 1983 [GB] United Kingdom ............... 8306785
Nov. 23, 1983 [GB] United Kingdom ............... 8331279

[51] Int. Cl.$^5$ .................. C12P 19/04; C12P 19/14; C12P 15/00
[52] U.S. Cl. ......................... 435/101; 435/99; 435/274
[58] Field of Search ............... 435/101, 172.3, 255, 435/99, 274; 536/18.5, 114, 52

[56] References Cited

U.S. PATENT DOCUMENTS

4,332,894 6/1982 Whistler ............... 435/101

FOREIGN PATENT DOCUMENTS

475836 5/1975 Australia ............... 536/114

OTHER PUBLICATIONS

McCleary et al, *Prog. Fd. Nutr. Sci.*, vol. 6, pp. 109–118, 1982.
Sigma Catalog, 1988, p. 611.
McCleary et al, "Effect of enzymatic modification on the solution and interaction properties of galactomannans", *Chem. Abstracts*, vol. 97, No. 23 (1982) Abst. No. 196970m.
McCleary, "Hydrolysis of legume seed D-galacto-D-mannans by α-D-galactosidases and β-mannanases" *Chem. Abstracts*, vol. 95, No. 5, (1981) Abst. No. 37750g.
Effect of Galactose Content on the Solution and Interaction Properties of Guar and Carob Galactommans, Carbohydrate Research, Elsevier Scientific Publishing (1981) vol. 92, pp. 269–285.
Enzymatic Modification of Locust Bean and Guar Gums, Hardev S. Dugal and John W. Swanson, Indian Pulp and Paper Technical Association, Jan., Feb., & Mar. 1974, vol XI, No. 1, pp. 29–35.
McCleary, Carbohydrate Research, Elsevier Scientific Publishing, 1979, vol. 71, pp. 205–230.
Chem. Abstr. V. 83, No. 11, Sep. 8, 1975, 81769W. (IPPTA 1974 11(1) 29–31).
J. Biol. Chem. vol. 244, No. 11, Jun. 10, 1969.

*Primary Examiner*—Michael G. Wityshyn
*Assistant Examiner*—L. N. Leary
*Attorney, Agent, or Firm*—Cushman, Darby & Cushman

[57] ABSTRACT

The invention provides a process for reducing the galactose content of galactomannan by means of a substantially specific galactosidase enzyme preparation in which the galactomannan is incubated in the form of a hydrated preparation containing 2–70 percent by weight of galactomannan. Preferable this preparation contains 8–50 percent by weight of galactommanan. The process yields galactomannans with a reduced content of galactose of which those containing 15 to 19 percent of galactose are novel compound. These latter products are used with advantage in foodstuffs and cosmetic preparations.

8 Claims, No Drawings

PROCESS OF POLYSACCHARIDES

This is a continuation of application Ser. No. 07/399,445, filed on Aug. 28, 1989, now abandoned, which was abandoned upon the filling hereof which is a continuation of application Ser. No. 07/147,634, filed Jan. 25, 1988, abandoned; which is a continuation a application Ser. No. 07/022,571, filed Mar. 4, 1987, abandoned; which is a continuation of application Ser. No. 06/584,905, filed Feb. 29, 1984, abandoned.

This invention relates to the processing of polysaccharides, more in particular seed galactomannans. The polysaccharides can be processed in an isolated for or e.g. in the form of seed endosperm particles of a number of Leguminosae, in particular guar seed. Guar is *Cyamopsis tetragonolubus* and it is usually processed to yield guard gum containing guaran as the main polysaccharide constituent. Guaran is known to have a galactomannan structure with a main chain of 1–4 linked beta-D-mannopyranosyl units to which alpha-D-galactopyranosyl units are attached. Usually it contains 35–45% by weight of galactose units and 65–55% of mannose units. It is believed to have a molecular weight range of $16-22 \times 10^5$, as indicated by an intrinsic viscosity range of 12–16 dL/g, as demonstrated in Carbohydrate Research (Elsevier Scientific Publishing Company), 1982, Vol. 107, pp. 17–32. Guaran guar gum and guar seed are abundantly available, but in some applications its properties are inferior to the properties of another industrial gum viz. locust bean gum, which is obtained from locust bean (carob seeds). This gum, however, contains predominantly a galactomannan containing 20–25% by weight of galactose units and 80–75% by weight of mannose units. It has an intrinsic viscosity range of 9–12 dL/g indicating a molecular weight range of $11-16.10^5$ i.e. lower than of guar gum. Locust bean gum has more favourable properties, such as gelling properties, in particular with other polysaccharides, than guar gum has. A galactomannan similar to guaran is available from lucerne (*Medicago Sativa*). Galactomannan containing more than 45 i.e. up to 50% by weight of galactose is available from fenugreek (*Trigonella foenum-graecum*).

Locust bean gum is becoming more expensive and scarce, due to poor crops and because locust bean groves are generally not being replanted. Therefore, attempts have been made to improve the properties of guaran by removal of part of the galactose units from the mannan main chain. A process for the enzymatic hydrolysis of some of the galactose units from the main chain has been disclosed in U.S. Pat. No. 4,332,894 (Whistler), wherein the treatment of guar gum or guaran solutions, particularly a 1% by weight aqueous solution with the enzyme alpha-D-galactosidase is mentioned.

One earlier disclosure of enzymatic removal of galactose side chains from galactomannan, inter alia from guar is Phytochemistry (Pergamon Press), 1975 Vol. 11, pp 1187–1194, in particular pp 1191–1192, Table 3 and FIG. 2. This also demonstrates the necessity of having the alpha-galactosidase enzyme sufficiently free from contaminating chain-splitting enzyme (beta-mannanase). From the experimental part of this citation (p. 1193, righthand column) it is evident that 0.1% (w/w) solutions of galactomannan were treated with alpha-galactosidase enzymes. Another prior disclosure is Indian Pulp and Paper Technical Association, 1974, 11 (1), 29–31, a reference discussed below.

A further, more general, disclosure of the preparation of galactose-depleted guaran with improved interactive properties similar to those of locust bean gum is Abstracts of Xth International Carbohydrate Symposium, Sydney, Australia, Jul. 16, 1980.

For the work described above and for all previously published work on enzymic modification of galactomannans we are aware of, it has been standard practice to incubate enzyme with polysaccharide in solution at concentrations up to 1% (w/w) to maintain a homogeneous reaction mixture.

Finally there is the thesis of Charles Wesley Baker of Purdue University of 1973, in which the treatment of guaran solution with enzyme is described. On page 100 the treatment of 100 mg/ml of aqueous guaran solution is mentioned. Since non-depolymerized guaran does not form a solution at this concentration but rather a thick paste, this description, which is not an enabling disclosure, is discounted. Either the concentration quoted is an error, or the guaran was so depolymerized before dissolving that it no longer represents normal material available commercially or prepared by careful methods of polysaccharide chemistry. The thesis confirms on page 139 that guaran used was depolymerized because Table 6 reports an intrinsic viscosity for guaran of 6.12 dL/g; expected values for non-depolymerized material are 2–3 times this value i.e. about 15 dL/g.

High concentrations of polysaccharides (i.e. 30% w/w) have sometimes been employed in processes involving enzymic modification, in particular enzymic modification of starch. However, such processes described in the prior art involve enzymic degradation of the main chain of the polysaccharide with a dramatic decrease in viscosity and removal of gelling properties.

However, such enzymatic conversions at higher concentrations were the exception rather that the rule, because homogeneous conditions were required.

More in particular Indian Pulp and Paper Technical Association 1974 Vol. 11 pp 29–35 states that the rate of enzymatic removal of galactose from galactomannan decreases with increasing substrate concentration and also decreases at temperatures above 38° C. the activity would drop.

In the present case, partial enzymatic hydrolysis, of typically about half of the galactose but as a minimum 3% from galactomannan containing 20–50% preferably from weight of galactose, results in more interactive regions along the mannan chain and therefore more structure formation and gelation after hydrolysis.

It has now been found that hydrated preparations containing 2–70% by weight of galactomannan can be incubated with a substantially specific alpha-galactosidase enzyme preparation in order to reduce the galactose content of the galactomannan from a value between 35 and 45% by weight to a value between 10 and 30, preferably below 27% by weight. The interactive properties of the galactomannan are thereby considerably improved.

Preferably the starting aqueous galactomannan paste contains between 8 and 50% by weight of galactomannan, more preferably between 15 and 40% by weight. Between 2 and 20% galactomannan the preparations are pastes, above 20% they gradually become particulate and resemble fine bread crumbs. The modified galactomannan contains preferably between 13 and 25% by weight of galactose, more preferably between 15 and 19% of galactose. The latter seem to be novel substances with superior gelling properties. Molecular weights are preferably in the range from 1 to 2.5 millions. The percentages of galactose in the modified galactomannan were determined by analysis of the galactose content using the method described by B. V. McCleary in Lebensmittel Wissenschaft und Technologie Vol. 14 pp 188-191 (1981).

According to the present invention the galactomannan preparation is incubated with the galactosidase enzyme under such conditions that the enzyme removes only a proportion of the galactose units from the mannan backbone.

This is conveniently done by incubating the preparation normally at a temperature between 0° and 70° C., preferably between 40° and 60° C., either with the enzyme solution or with the enzyme added after hydration. Alternatively, enzyme powder can be mixed with a dry preparation of the polysaccharide before hydration.

The incubation can be carried out by mixing the ingredients i.e. galactomannan, water and enzyme e.g. in a twin screw extruder or colloid mill. The incubation is carried on until the galactose content of polysaccharide has reached the desired level. This usually lasts from a few hours to a few days.

The pH of the paste should be within the range of activity of the enzyme, usually between 4 and 6. Addition of some acid or buffer solution is sometimes desirable.

The enzyme preparation should have a substantially specific alpha-galactosidase activity and have at most only a weak beta-mannanase activity. After the incubation the galactomannan should consequently have a molecular weight not below two thirds of the original value. Suitable enzymes can be of vegetable origin (e.g. from lucerne, fenugreek, coffee beans or guar seed) or they can be obtained from bacterial (e.g. *Bacillus cereus, Escherichia coli*) or fungal cultures (e.g. *Aspergillus niger* or *Sacharomyces cerevisiae*).

After the removal of some i.e. about half of the galactose units from the galactomannan the enzyme is deactivated e.g. by heat treatment and dried by convential methods. Although it may be desirable to purify the modified galactomannan so as to remove free galactose and enzyme material e.g. by dissolving and precipitating the modified galactomannan, it is usually not neccesary to do so and the product can be used as such for various applications in which the gelling properties are important. In particular, it can be used in combination with other polysaccharides such as agar, carageenan and xanthan, taking advantage of the synergistic interaction with these materials.

The rheological properties of the modified galactomannan obtained according to the invention, in particular those containing between 15 and 19% by weight of galactose, are such that they are valuable ingredients for foodstuffs (human and animal), and also for cosmetic pharmaceutical and industrial applications.

For convenient processing it is recommendable in some instances to prepare beforehand intimate or rather homogeneous mixtures of at least one emulsifier and/or other polysaccharide with enzymatic modified galactomannan. These mixtures may contain an amount of emulsifier at least equal to the weight of modified guar and other gums, if any. The combinations are conveniently prepared from solutions or melts using techniques such as spray-drying, spray-cooling or drum-drying.

EXPERIMENT 1

Action of Purified Alpha-galactosidase on Depolymerised Guar Galactomannan (Guaran Beta-mannanase Limit Galactomannan)

Aim

This experiment was performed to determine the effect of substrate concentration on the rate of release of D-galactose from guar galactomannan by alpha-galactosidase enzyme. Partially depolymerised guar galactomannan (guar beta-mannanase limit galactomannan) was employed in these experiments to minimise viscosity effects.

Guaran beta-mannanase limit galactomannan (GMLG, 0.2 mL 0.2-10% w/w) in sodium acetate buffer (0.1M, pH 4.5) was incubated with guar seed alpha-galactosidase II* (0.1 mL, 13 n kat on p-nitrophenyl alpha-D-galactopyranoside) for 5 min. at 40° C. The reaction was terminated and the increase in reducing sugar level was monitored as a measure of the degree of hydrolysis. The results are shown in Table I and it is obvious that for the enzyme to work at maximal rate a substrate concentration in excess of 10% w/w (100 mg/mL) is required).

*ref. McCleary B. V. (1983) Phytochemistry 22 pages 649–658.

Similar results were obtained when an alpha-galactosidase from *Aspergillus niger* was employed. Increasing the substrate concentration from 0.2 to 10% w/w gave an approx. ten-fold increase in activity.

TABLE I

| Concentration of substrate % w/w | Enzyme Activity % of maximum |
|---|---|
| 0.2 | 4.4 |
| 0.5 | 9.5 |
| 1.0 | 14.5 |
| 2.5 | 30.5 |
| 5.0 | 71.5 |
| 10.0 | 100.0 |

This experiment provides data on the optimal substrate concentration to maximise hydrolysis without the probably modifying effects of excessively high viscosity. The effect of viscosity will become more apparent in the other examples provided, in which native guar galactomannan was employed.

EXAMPLES 1 AND 2

Guar flour (100 g) was extracted with boiling aqueous ethanol (80% v/v) and the suction-dried flour added to ice-cold water (3 L) with rapid blending in a Kenwood mixer. The paste was allowed to stand for 2 hours and then mixed in a Waring Blender (in batches). The paste was heated to 60° C. and reblended with the Kenwood mixer.

Samples of the above paste (465 g containing 15 g of guar flour i.e. 3.2% w/v) were taken and treated as follows:

A. To the paste sample was added guar alpha-galactosidase II (3 mL, 720 n kat on p-nitrophenyl alpha-D-galactopyranoside) plus sodium acetate buffer (2.40 mL, 2M, pH 4.5) and the mixture was incubated at 37° C. for 24 h in the mixing bowl of a Farinograph. The paste was mixed for 15 min. every 2 hours for the first 8 hours.

The reaction was terminated by heating the reaction mixture to 80° C. and polysaccharide was recovered by alcohol precipitation. The precipitate was washed with ethanol, acetone and ether and dried in vacuo.

A sample of the dried material was dissolved in water and centrifuged, and galactomannan polysaccharide was precipitated with alcohol. The purified polysaccharide had a galactose/mannose ratio of 25:75 and a specific viscosity of 17.6 dL/g (cf. value for the original galactomannan of 17.7 dL/g, and a galactose/mannose ratio of 40:60).

B. To guar paste (465 g, 3.2% w/v as above) were added guar alpha-galactosidase II (2 mL, 480 n kat) plus sodium acetate buffer (3 mL, 2M, pH 4.5) and water (41 mL). The paste was mixed thoroughly using a spatula and incubated at 40° C. for 48 hours without further mixing. The reaction was terminated by treating the paste at 100° C. for 10 min. and the polysaccharide (and a sample of purified galactomannan) prepared as above. The purified galactomannan had a galactose/mannose ratio of 24:76 and a specific viscosity of 17.6 dL/g).

EXAMPLE 3

Ethanol-washed guar splits (40 g) were allowed to imbibe in distilled water (600 mL) at 40° C. for 4 hours and then at 80° C. for 2 hours. The material was then mixed in a Farinograph bowl and more water (100 mL) was added.

Acetate buffer (4 mL, 2M, pH 4.5) plus guar alpha-galactosidase II (6 mL, 1440 n kat) plus water (17 mL) were added with mixing. The concentration of guar splits was 5.5% (w/v). The paste was mixed 4 times (for periods of 5 min.) over the next 8-hour-period and left unstirred overnight (at 37° C.) in the Farinograph bowl. The paste was mixed again and incubated for a further 24 hours (total incubation time 48 hours). The galactomannan in an aliquot of this paste was purified and the remaining paste was treated with alcohol and dried by solvent exchange. The purified galactomannan had a galactose/mannose ratio of 23.5:76.5 and a specific viscosity of 14.0 dL/g.

EXAMPLES 4 and 5

Guar splits were milled to pass a 2 mm sieve and extracted with boiling ethanol. The flour (30 g) in water (180 mL) was heated in a boiling water bath for 10 min. and then stored at 40° C. for 20 hours. The heterogeneous paste was divided into two equal batches and treated as follows:

A. One batch of paste (105 g) was placed in the mixing bowl of a Farinograph and the following solutions were added: guar alpha-galactosidase II (2 mL, 480 n kat); sodium acetate buffer (3 mL, 2M, pH 4.5); and water (5 mL). The final concentration of flour in water was 15% w/v. The paste was mixed and incubated at 40° C. for 48 hours.

B. The second batch of paste was treated in the same way as the first, except that the amount of added water was 55 mL (cf. 5 mL for batch A). The final concentration of this paste was 10% w/v. The paste was mixed and incubated at 40° C. for 48 hours.

The reactions were terminated by incubation of the pastes at 100° C. for 10 min. A sample of each paste was removed and galactomannan was extracted for analysis. The bulk of the sample was freeze-dried. The purified galactomannans (samples A and B) both had galactose/mannose ratios of 27:73 and specific viscosities of 19.8 dL/g.

EXAMPLE 6

Effect of beta-mannanase contamination in alpha-galactosidase preparations on the properties of alpha-galactosidase-modified guar galactomannan.

Guar pastes prepared as described in Example 1 were used. Guar flour paste (3.2% w/v, 155 mL) was incubated with guar alpha-galactosidase II (0.5 mL, 240 n kat) plus sodium acetate buffer (5 mL, 2M, pH 4.5) at 37° C. for 20 hours. The reaction was terminated by treating the pastes at 100° C. for 10 min. and galactomannan was purified and dried by solvent exchange (ethanol, acetone, ether) and vacuum desiccation. The levels of beta-mannanase used were 0 n kat (sample A); 0.025 n kat (sample B); 0.25 n kat (sample C); and 2.5 n kat (sample D). Beta-mannanase activity was standardised using carob galactomannan (0.2% w/v) in sodium acetate buffer (0.1M, pH 4.5) as substrate. The galactose/mannose ratios of each of the samples was 19:81 and the specific viscosities were 16.54 dL/g (A); 16.21 dL/g (B); 14.34 dL/g (C); and 4.79 dL/g (D). These results demonstrate that under conditions of high substrate concentration a galactomannan with a galactose/mannose ratio about that of locust-bean galactomannan and an equivalent to slightly better viscosity can be prepared from guar galactomannan using guar alpha-galactosidase contaminated to an extent of up to at least 0.1% by beta-mannanase. 1% beta-mannanase contamination (sample D) caused significant depolymerization.

EXAMPLE 7

Guar flour (1 kg) was extracted with boiling aqueous ethanol (80% v/v) for 10 min. and free liquid was removed by suction. The flour was added to the mixing bowl of a Hobart Mixer containing ice cold water (10 L). The mixer was run on setting I and the flour was added slowly to minimise formation of lumps. As the paste began to thicken, a further aliquot (10 L) of ice-cold water was added in portions. The paste was mixed for a further 10 min. with the machine on setting 3, and was then left overnight to allow complete hydration. The paste was further mixed (setting 3) and guar alpha-galactosidase II (20 microkat) in sodium acetate buffer (pH 4.8, 100 mL) was added with thorough mixing. The bowl and contents were sealed with plastic wrap and incubated at 37° C. for 48 hours. The reaction was terminated by heating the paste to 80° C. employing a steam jet and the paste was freeze-dried. The guar flour thus treated contained guaran with a galactose/mannose ratio of 18:82.

EXAMPLE 8

Ice creams were prepared according to the following formulation in a 40 L small-scale pilot plant:
10% non-fat milk solids
10% fat
15% sucrose
0.3% emulsifier
0.2% stabilizer
64.5% water The stabilizer was (1) guar gum or (2) locust bean gum or (3) alpha-galactosidase-modified guar gum from Example 7.

The ice cream was packed in 0.5 L blocks and its melting characteristics were measured at 15° C. The results are given in Table II.

TABLE II

| No. | Stabilizer | Galactose/Mannose ratio of stabilizer | Drip rate of ice cream (mL/h) | Shape retention of ice cream after 4 h |
|---|---|---|---|---|
| 1 | Guar gum | 40:60 | 40 | poor |
| 2 | Locust bean gum | 23:77 | 21 | good |
| 3 | Modified guar gum | 18:82 | 20 | very good |

As shown in Table II, the incorporation of alpha-galactosidase-modified guar gum, with a galactose content similar to that of locust bean gum, instead of locust bean gum, into ice cream resulted in the ice cream having equal to superior characteristics as compared with the ice cream containing locust bean gum as stabilizer. The drip rate of the ice cream containing alpha-galactosidase-modified guar gum was similar to that of the ice cream containing locust bean gum, but its shape retention after 4 hours at 15° C. was noticeably better. The ice cream containing unmodified guar gum was markedly inferior, both in drip rate and shape retention, to the ice creams containing the other stabilizers. These results demonstrate that the alpha-galactosidase-modified guar gum produced by enzyme incubation in a thick paste is at least equal to native locust bean gum in its functional properties.

EXAMPLE 9

Mixtures of xanthan (0.5%, w/v) and galactomannan (1.0%, w/v) in water were prepared as follows: The constituents were dispersed in water in a screw-top bottle using a top-drive Atomix, autoclaved for 5 min. at 120° C., remixed with the Atomix, centrifuged (3,000 rpm, 2 min.) to remove bubbles, warmed in a water bath to re-melt, and finally poured into perspex moulds of 0.5 inch diameter by 0.48 inch deep. Yield stress was measured on the gel plugs, at room temperature, after ageing for 24 h., using an Instron Materials Tester. Samples were compressed between parallel plates using a crosshead speed of 20 mm/min. The galactomannan used was (1) guar gum or (2) locust bean gum or (3) alpha-galactosidase-modified guar gum from Example 3, or (4) alpha-galactosidase-modified guar gum from Example 7.

The results are given in Table III.

TABLE III

| No. | Galactomannan | Galactose/Mannose ratio | Yield stress (N) |
|---|---|---|---|
| 1 | Guar gum | 40:60 | no gel formed |
| 2 | Locust bean gum | 23:77 | 3.3 |
| 3 | Modified guar gum | 23.5:76.5 | 3.0 |
| 4 | Modified guar gum | 18:82 | 5.3 |

The interaction of modified guar gum with xanthan is similar to the interaction of locust bean gum with xanthan, and unlike that of guar gum, which does not form gels. Similar results have been obtained for interactions of galactomannans with agarose.

EXAMPLE 10

Guar splits were treated to destroy aleurone cells and contaminating microorganisms by boiling in aqueous ethanol (80%, v/v) for 10 min. Free liquid was decanted and the splits air dried. The sterilised splits were treated by one of the following methods.

Method A

Splits (10 g) were mixed with water to give the solids contents indicated in Table IV. After 30 min. to allow uniform hydration the splits were ground first in a mincer attachment of a Kenwood Chef. and finally in a colloid mill (E. Zehnder, Zurich), to give fine powders. Solutions of Guar alpha-galactosidase II were then sprayed on to the powder to give final solids contents and enzyme dosages indicated in Table IV. The mixture was incubated at 40° C. and extent of reaction monitored by increase in reducing power. After about 48 hrs, reaction was terminated by heating to 100° C. The galactose/mannose ratios of the products is shown in Table IV.

TABLE IV

| No. | Initial Hydration (wt. % solids) | Final Hydration (wt. % solids) | Enzyme Dosage (nkat/g. guar) | Final Galactose: Mannose Ratio |
|---|---|---|---|---|
| 1 | 30 | 20 | 34 | 34:66 |
| 2 | 30, 40 and 50 | 20 | 340 | 21:79 |
| 3 | 40 and 50 | 30 | 340 | 29:71 |
| 4 | 40 | 30 | 510 | 16:84 |
| 5 | 50 | 35 | 680 | 21:79 |
| 6 | 50 and 60 | 40 | 680 | 23:77 |
| 7 | 50 | 45 | 680 | 24:76 |
| 8 | 60 and 60 | 50 | 680 and 850 | 31:69 |

Method B

Splits (10 g) were mixed with Guar alpha-galactosidase II solution to give the solids contents and enzyme dosages indicated in Table V. After 30 min. to allow uniform hydration, pastes at 20% solids were homogenised with a Silverson Laboratory Mixer; at higher solids contents the hydrated splits were milled as in Method A except that dry ice was added to prevent heat inactivation of the enzyme. Incubations were carried out as for Method A and the galactose/mannose ratios of the products is shown in Table V.

TABLE V

| No. | Hydration (wt % solids) | Enzyme Dosage (nkat/g. guar) | Final Galactose/Mannose Ratio |
|---|---|---|---|
| 1 | 20 | 34 | 37:63 |
| 2 | 20 | 340 | 25:75 |
| 3 | 25 | 340 | 27:73 |
| 4 | 30 | 340 | 30:70 |

EXAMPLE 11

The procedure for Example 10, Method A, Experiment No. 6 was repeated except that the temperature of the incubation was varied from 40° C. The galactose content of the galactomannan during the course of the incubation is shown in Table VI.

TABLE VI

| Temperature (° C.) | % Galactose in Galactomannan after | | | | |
|---|---|---|---|---|---|
| | 0 hrs. | 7 hrs. | 24 hrs. | 31 hrs. | 48 hrs. |
| 40 | 38 | 30 | 26 | 24 | 23 |
| 50 | 38 | 31 | 25 | 24 | 21 |
| 55 | 38 | 25 | 21 | n.d.* | n.d.* |
| 60 | 38 | 28 | 28 | 28 | 28 |

*n.d. = not determined

EXAMPLE 12

Guar flour, solutions of guar α-galactoside II, and water were mixed to give the solids contents and enzyme dosages given in Tables VI-VIII. Each sample had a final weight of about 10 g. The mixtures were stirred rapidly using a spatula until they resembled fine bread crumbs and the guar was uniformly hydrated. Incubation was at the temperatures indicated below and samples of 100 mg were withdrawn at the times shown and the reaction terminated by heating to 100° C. The galactose/mannose ratios in the polysaccharide were then determined.

A. The effect of temperature on the reaction was studied using a guar flour concentration of 40% (w/w) and an enzyme dosage of 850 nkat/g. guar.

TABLE VI

| No. | Temperature (°C.) | % Galactose in Galactomannan after | | | | |
|---|---|---|---|---|---|---|
| | | 0 hr | 1.5 hr | 3 hr | 5 hr | 23 hr. |
| 1 | 37 | 38 | n.d. | n.d. | 22 | 2 |
| 2 | 55 | 38 | 20 | 13 | 3 | n.d. | n.d. = not determined

These results demonstrate that the reaction proceeds much more quickly at 55° C. than at 37° C.

B. The effect of guar concentration on the reaction was studied at 55° C. and an enzyme dosage of 850 nkat/g guar.

TABLE VIII

| No. | Guar concentration (%, w/w) | % Galactose in Galactomannan after | | | | | |
|---|---|---|---|---|---|---|---|
| | | 0 hr | 1.5 hr | 3 hr | 5 hr | 7 hr | 23 hr |
| 1 | 40 | 38 | 20 | 13 | 6 | 3 | n.d. |
| 2 | 50 | 38 | 25 | 21 | 17 | 14 | n.d. |
| 3 | 60 | 38 | 33 | 32 | 32 | 32 | 31 |
| 4 | 70 | 38 | 36 | 36 | 36 | 36 | 35 | n.d. = not determined

These results demonstrate that above 40% guar the reaction slows down, but even at 70% guar some galactose is removed very slowly.

C. The effect of enzyme dosage on the reaction was studied at 40% (w/w) guar concentration and 55° C.

TABLE IX

| No. | Enzyme Dosage (nkat/g. guar) | % Galactose in Galactomannan after | | | | | |
|---|---|---|---|---|---|---|---|
| | | 0 hr | 1.5 hr | 3 hr | 5 hr | 7 hr | 23 hr |
| 1 | 250 | 38 | 29 | 24 | 20 | 18 | 4 |
| 2 | 500 | 38 | 26 | 20 | 14 | 11 | n.d. |
| 3 | 850 | 38 | 20 | 13 | 6 | 3 | n.d. | n.d. = not determined

These results demonstrate that the rate of reaction drops with lower enzyme dosages.

EXAMPLE 13

Alpha-galactosidases from the germinating seeds of lucerne (*Medicago sativa*) and fenugreek (*Trigonella foenum-graecum*) were compared to alpha-galactosidase II from germinating guar seeds. All experiments were carried out using guar flour at 40% guar concentration, 55° and 250 nkat alpha-galactosidase per gram guar as described in Example 12. All enzyme preparations were free of beta-mannanase.

TABLE X

| No. | Source of alpha-galacto sidase | % Galactose in Galactomannan after | | | | | |
|---|---|---|---|---|---|---|---|
| | | 0 hr | 1.5 hr | 3 hr | 5 hr | 7 hr | 23 hr |
| 1 | guar | 38 | 29 | 24 | 20 | 18 | 4 |
| 2 | lucerne | 38 | 33 | 29 | 27 | 26 | 19 |
| 3 | fenugreek | 38 | 30 | 27 | 24 | 22 | 12 |

These results demonstrate that all three enzymes are capable of removing galactose from guar galactomannan, but in the conditions used the enzyme from germinating guar has the fastest reaction rate.

We claim:

1. In a process for reducing the galactose content of guar gum containing a galactose:mannose weight ratio in the range of 20:80 to 50:50, the improvement which comprises incubating at a pH of 4 to 6 a hydrated preparation containing 8 to 50 percent by weight of guar gum with alpha galactosidase until the galactose:mannose weight ratio is between 10:90 and 27:73.

2. A process according to claim 1, wherein the hydrated preparation contains from 25 to 40 percent by weight of guar gum.

3. A process according to claim 1 wherein the incubation is stopped at a galactose:mannose weight ratio between 13:87 and 25:75.

4. A process according to claim 1 wherein the incubation is stopped at a galactose:mannose weight ratio between 15:85 and 19:81.

5. A process according to claim 1 wherein the molecular weight of the galactose depleted guar gum has a value of at least two thirds of the molecular weight of the starting guar gum.

6. A process as claimed in claim 1, wherein the alpha galactosidase is produced by a plant selected from the group consisting of guar, lucerne and fenugreek.

7. In a process for reducing the galactose content of guar gum containing a galactose:mannose weight ratio in the range of 20:80 to 50:50, the improvement which comprises incubating at a pH of 4 to 6 a hydrated preparation containing at least 20 percent by weight of guar gum with alpha galactosidase until the galactose:mannose weight ratio is between 10:90 and 27:73.

8. A process according to claim 1 wherein the hydrated preparation contains 20 to 40 percent by weight of guar gum.

* * * * *